United States Patent [19]

Edwardson et al.

[11] Patent Number: 4,973,114
[45] Date of Patent: Nov. 27, 1990

[54] SYSTEM FOR PRODUCING HOLOGRAMS

[75] Inventors: Svante R. Edwardson, Solna; Rolf Eriksson, Hagersten, both of Sweden

[73] Assignee: Dentatus International AB, Hagersten, Sweden

[21] Appl. No.: 439,467

[22] Filed: Nov. 21, 1989

[51] Int. Cl.$^5$ .............................................. G03H 1/22
[52] U.S. Cl. .................................. 350/3.83; 350/3.6; 356/347
[58] Field of Search ........................ 350/3.6, 3.8, 3.83, 350/3.84; 372/101; 356/347

[56] References Cited

U.S. PATENT DOCUMENTS

| | | |
|---|---|---|
| 3,631,711 | 1/1972 | Kreuzer . |
| 3,644,047 | 2/1972 | Brown et al. . |
| 3,721,498 | 3/1973 | Narodny et al. . |
| 3,744,911 | 7/1973 | Stetson et al. . |
| 3,975,101 | 8/1976 | Copeland . |
| 3,976,383 | 8/1976 | Olsen . |
| 4,071,291 | 1/1978 | Suzuki et al. ......................... 350/3.8 |
| 4,206,965 | 6/1980 | McGrew ............................. 350/3.84 |
| 4,764,012 | 8/1988 | Ryden et al. . |
| 4,798,466 | 1/1989 | Bouteyre et al. .................... 356/347 |

OTHER PUBLICATIONS

"Holographic Measuring of Deformations in Complete Upper Dentures", Optics and Photonics Applied to Medicine, vol. 211, 1979, By I. Dirtoft et al., pp. 106–110.

Primary Examiner—Bruce Y. Arnold
Assistant Examiner—J. P. Ryan
Attorney, Agent, or Firm—Young & Thompson

[57] ABSTRACT

An apparatus for making holograms of an object is described. The apparatus has a laser source emitting a collimated or slightly divergent laser beam, and a holder for a holographic plate to hold the holographic plate between said object and said laser source in a position near said object. A positive lens means having its focus is placed between said lens means and said holographic plate such that a divergent laser beam is impinging on said holographic plate and cover an illuminating area on said plate extending well beyond the area of said object in a plane parallel to said holographic plate. A closed housing is placed around said laser source and said lens means, which housing has a controllable shutter to be opened only at control provided in an end wall in a position cutting the beam path of said outgoing laser beam.

12 Claims, 3 Drawing Sheets

SYSTEM FOR PRODUCING HOLOGRAMS

TECHNICAL FIELD

This invention relates to a system for producing holograms especially suited for three dimensional measurements of objects which tend to have a part changing its position in the course of time. The invention is particularly deviced for providing holograms adapted for making measurements on dental casts.

DESCRIPTION OF THE PRIOR ART

Changes in the rows of teeth have often been examined by making measurements on plaster models. Many different aids have been used for these measurements, such as rulers, callipers, dividers, symmetrographs and clear plastic arch form overlays with millimeter scales. Measurements have sometimes been made directly on the plaster model, sometimes on a photography or on an impression of the same. Three dimensional measurements have sometimes been made by aid of particular measuring apparatuses. As computerization has become such a common technique nowadays an increasing amount of measuring points has been used in the course of time. All such measurements are made on one model at the time. The precision at measurements of this kind is in the order of tenths of millimeters. The model to be compared with a previous model is adjusted on place by aid of reference points.

In the recent years measurements have been made by making use of holograms taken on dental casts. In an article "Tooth position measurements on dental casts using holographic images" by H. Rydén et al, published in American Journal of Orthodontics 1982; 81:310–313 a laser measuring technique is described in which both rows of teeth are seen at the same time which gives a very illustrative picture of changes which have taken place.

In an article "Holographic measuring of deformations in complete upper dentures" by I. Dirtoft et al, SPIE Vol 211 Optics an Photonics Applied to Medicine, 1979 a method is described in which measurements are made on sandwich holograms put together by holograms taken at different times.

In U.S. Pat. No. 4,764,012 a device for determining the displacement of a tooth between two different examinations made at separate occations. According to this document comparations are made between a hologram taken by a plaster dental cast taken at a first time and a plaster dental cast taken at another time or a hologram of it.

OBJECTS OF THE INVENTION

An object of the invention is to provide a device for making holograms on objects to be measured without the need of having particularly vibration free arrangements for the device.

Another object of the invention is to provide a combination device in which the hologram or holograms of an object to be measured are taken, and also in which three dimensional measurements on the object are made by aid of the hologram and the object or a model of it or by aid of at least two holograms.

Even though making holograms of dental cast is described and illustrated in the description it is obvious for a man skilled in the art that the same idea is applicable also for making holograms of other objects.

BRIEF DESCRIPTION OF THE DRAWINGS

Further features and details of the invention will be apparent from the following description of certain modes of operation and a specific embodiment of the invention that will be given by way of example with reference to the accompanying drawings, in which.

DESCRIPTION OF THE DRAWINGS

Figure 1:
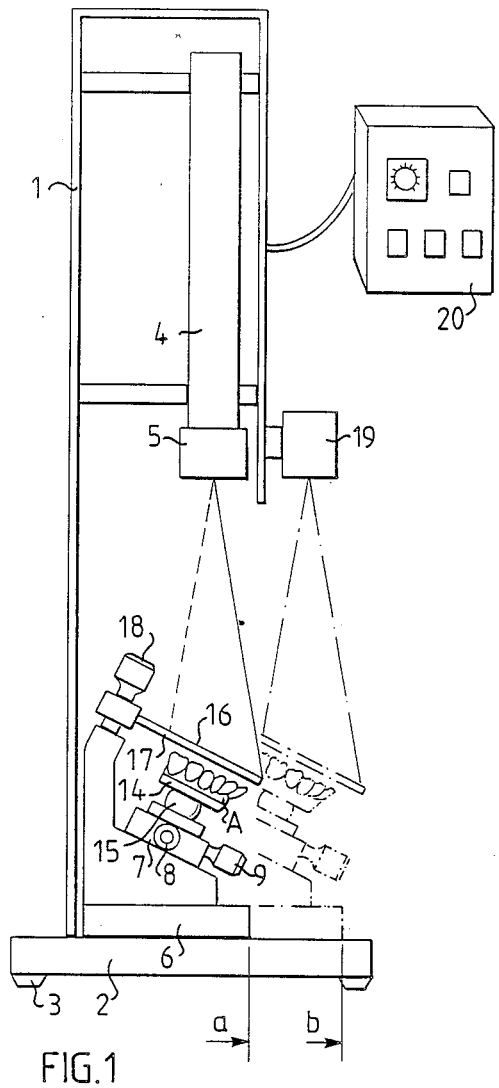
FIG. 1 is a side view having the side wall taken away of an embodiment of the device according to the invention.

With reference to FIG. 1, the apparatus is mounted inside a cover 1. The cover is vertically arranged on a base plate 2 resting on four shock absorbing, elastic pads 3. The cover is made of a stiff material, such as aluminum, and the base plate is made of a material and has such a thickness that the apparatus in spite of being rather high has a low point of balance, e.g. is made of steel. A laser tube 4, e.g. a 5 mW helium-neonlaser tube, with optics and a shutter unit 5 is rigidly mounted inside the cover 1. The laser tube and the optics are preferably placed physically in a row after each other in order to prevent the use of mirrors folding the beam path. All optical elements can have small scratches and dust particles causing light to diffract, resulting in noticeable patterns in the beam, and therefore as few optical elements as possible are to be used. This makes the housing 1 rather high. However, it lies within the scope of the invention to place the laser at the side of the optics and directed upwardly and to use folding mirrors to direct the laser beam through the optics (not shown). The elements 4 and 5 are not bound to be directed exactly vertical but could be obliquely provided in the casing 1 with an acute angle to the vertical.

Figure 2:
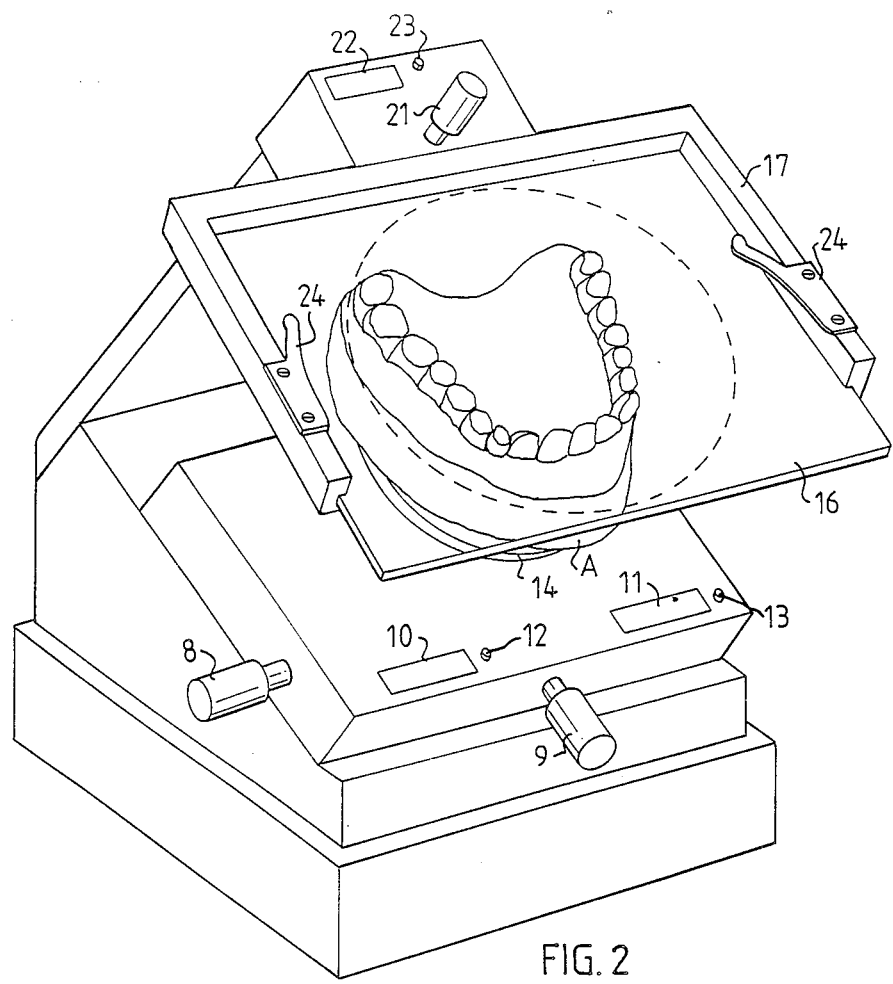
FIG. 2 is a perspective view in a wider scale than in FIG. 1 of an embodiment of a support frame provided in the device according to the invention.

On a support 6 mounted on the base plate 2 a coordinate table 7 is arranged, permitting measurement along the cartesian coordinates, i.e. the x-, y- and z-axes in relation to a holographic plate 16 placed in a holder 17. In the embodiment shown, the adjustments along the x- and y-axes are made by means of knobs 8, 9 on the coordinate table 7 and the result of the movements in the different directions are shown on displays 10, 11, respectively (see FIG. 2) The movement in the z-direction is provided by moving the holographic plate 16 along the z-axis by means of a knob 18, the result being shown on a display 22. Means to monitor the turning of a knob to provide a result of the movement on a display are common in the art and a thorough description and an exact design of this means are therefore not provided. The displays are preferably zero adjustable by means of some set means 12 and 13, respectively, and the displays are chosen to provide a good resolution, preferably in the order of 0.01 mm. Orientation and stabilisation of the object A is achieved by using a holder 14 mounted on a ball and socket joint 15. The holographic plate 16 is mounted in the frame 17 and is locked in place above the object A. As mentioned above, the frame 17 is adjustable to have a desirable distance to the object A by means of a knob 18.

The support surface of the support 6 for the coordinate table 7 is oblique in order to have the object A and the hologram 16 are obliquely mounted (the x-, y-, z-coordinate system is of course oblique as well). The reason for this is that the device according to the invention also is intended for making the comparing examination of the hologram of a cast taken at a first time and a cast or a hologram of it made at another time. The obliquity of the mounting is chosen such that the observer shall have a comfortable view of the area to observe and also so that light reflections of a lamp 19 lightening the hologram (and the observation area) shall not be disturbing. This means that the viewers eye preferably shall be positioned in or near the bisectrice of the angle between the impinging and the reflected beam.

As shown in dashed lines in FIG. 1 the support having the coordinate table 7 is mounted on the base plate 2 to be slidingly movable towards an operator from a back position marked a to a front position marked b. The holograms are taken when the support 6 is in its back position and the holograms are observed when the support 6 is in its front position. The lamp 9 is provided outside the housing 1 in a position corresponding to the position of the shutter unit 5 in a way which will give the same features as the exposure of the hologram made by the elements 4 and 5, i.e. parallel to the elements and giving practically the same divergent beam path. The lamp 9 is thus placed in a plane perpendicular to the moving direction of the holder 6 and at the same distance from the elements 4, 5 as the distance between a and b.

Figure 3:
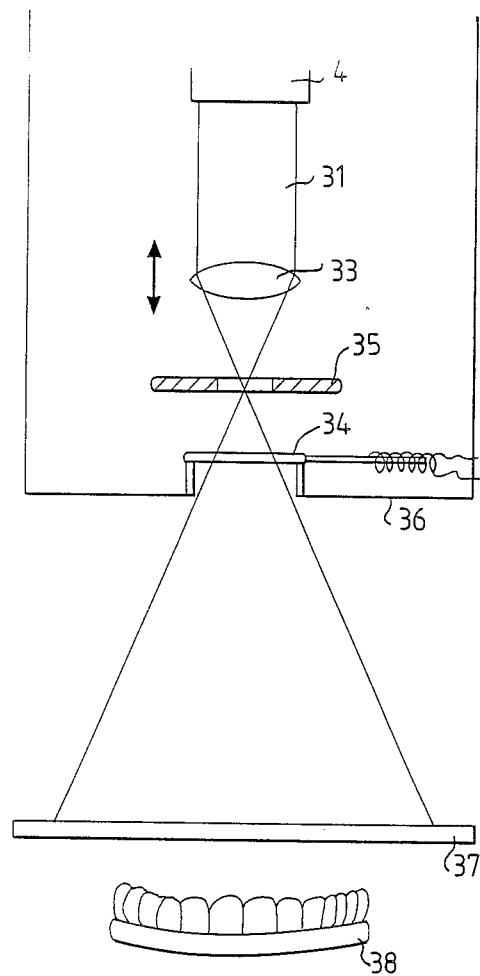
FIG. 3 is a schematic view of the optic arrangement when the device according to the invention is set for providing a hologram.

Referring to FIG. 3, in which the optical system is shown, the collimated laser beam 31 from the laser 4 is converged by a lens 33 having a focus situated between the lens and the object. The lens 33 may be a convex lens as shown in FIG. 3, but it may also (preferably) be a gradient-index lens (not shown). The laser 4 and the lens 33 are provided in a normally closed housing sealed against the environment in order to prevent dust form entering into the housing 32 of the optics. A solenoid controlled shutter 34 is provided on the optical axis at an output for the beam from the housing. Solenoid controlled devices are rather common and therefore the shutter control is only shown schematically. Preferably, the shutter 34 is provided in the bottom of a cupformed cavity formed in the end wall 36 of the housing in order to prevent dust from streaming into the housing at the short times when the shutter is opened.

As an extra precaution to keep the inner of the housing free from dust a small overpressure may be provided in the housing. This over pressure may be provided by having an inlet with dust free air (not shown). The inlet could then be positioned such that the air stream is streaming over the surface of the lens taking possible dust particles off the surface.

The focus of the lens 33 is preferably situated inside the housing such that the outgoing beam from the housing is divergent. The inner walls of the housing are painted with a dull black colour in order to prevent inner reflexions. In order to stop possible strap light from the laser a diaphragm 35 could be placed at the beam focus, but it has experimentally been proven that it is not necessary to have a diaphragm. However, if a diaphragm is provided the aperture of the diaphragm must have a size well around the focal point and must not be a pinhole. A pinhole diaphragm demands a very exact adjustment before each exposure of a hologram and makes the device very sensible for possible vibrations, which must be avoided. Since no pinhole is placed in the focus, the exposure time can be chosen to be rather short, i.e. around 2 sec. to be compared to 20 sec. usually necessary when using a pinhole. The short exposure time is believed to be the reason why the exposures taken with the invention device at an experimental arrangement have had such a good quality. Experiments made by the inventors have shown that good quality holograms are easily providable using the optics shown in FIG. 3 also without the diaphragm 35.

The holographic medium 16, preferably an emulsion coated glass plate, is placed in the divergent beam path. The lens position can be controlled such that the beam is covering an area around the dental plaster cast A provided a small distance below the holographic film 16. The lens position is adjustable such that the outgoing beam not only covers the cast but also an area well around it, for instance could the beam at the cast have a diameter 1.5 times the diameter of the cast itself. The inventors have discovered that possible dust particles on the lens have their greatest influence near the edges of the holographic plate.

An exposure of a hologram is made in the following way. The dental cast is stabilised on the adjustable holder 15. Correct orientation of the cast is facilitated by a jig (not shown) temporarily fitted to the holder 17. Three "reference teeth" are selected having the greatest possible mutual affort and having a location for which changes are rare. The jig includes movable arms (not shown), which are adjusted so as to rest against the reference teeth of the cast. In this position the joint 15 is locked. The model can then be translated without changing its vertical setting. The operator may have a lot of jigs in order to have a jig for each work under operation, i.e. for each work where a hologram of a first cast has been taken waiting for the next cast to be taken and compared with the hologram of the first cast. In stead of having several jigs to his disposal the operator may have a jig provided with scales easy to read and make a note of the adequate adjustment for the cast in question, or the operator may have several jigs provided with scales to his disposal.

When the orientation is satisfactory the jig is removed. Under dark room lighting an unexposed holographic plate 16 is placed into the holder 17 held by clamps 24 and exposed to the laser using an exposure control 20.

If two holograms of the same object taken at different times are to be compared with each other the upper hologram has to be exposed somewhat further away from the cast than the lower hologram. This allows the holographic images to be superimposed without the plates touching each other. The distance between the plates is dependent on the desired measuring range along the z-axis adjusted with the knob 21 and read on the display 22. A separation of 3 mm was chosen in a study.

For comparative measurement of the cast and hologram the cast is stabilized using the adjustable jig, as described above. When the reference points on the model and the hologram coincide all displays 10, 11, 22 are set to zero using the reset knobs 12, 13, and 23, respectively. The cast is then translated by turning the knobs 8, 9 on the coordinate table 7 until the desired cast and hologram measuring points are superimposed. The x-, y- and z-axes reading shown on the displays 10, 11, 22 represent the deviations between the cast and the hologram.

For comparison between two holograms the cast is replaced by a hologram placed lower than the hologram to which it is to be compared. The lower hologram is thus placed such that it can be moved along the coordinates using the knobs 8, 9 and 21. Measurements are then performed as previously described for the cast and hologram.

After the exposure of a hologram the exposed plate is transferred to a developing unit under dark room conditions. In order to improve visibility when two holograms are to be compared to each other one of the holograms can be given a couloured shade, for instance a green shade can be given by using a bleach which shrinks the gelatin layer of the plate. This reduces the wave length of the reflected light from the image thus producing the green shade. Preferably, the upper hologram is prepared in this way. When using a HeNe-laser a red hologram is provided and thus the lower hologram is red. This change of the wave length may affect the results in the z-axis but not in the x- and y-axes. It is easier to superimpose two holograms of different colours. Experiments have shown that there were no noticeable difference in the results of the comparations between the holograms if the holograms were of the same colour or if a green hologram was placed above a red one or vice versa.

The unique advantage with the holographic method according to the invention, is the possibility of providing holograms of dentitions at different times under the same circumstances and to be able to make the comparing measurements using the same equipment as is used when taking the holograms. Changes in a tooth position can be visualized and measured with the two dental arches superimposed upon each other in a way very comfortable for the observer. The vertical extension of the apparatus makes it easy to have in a laboratory because it is not area consument.

We claim

1. An apparatus for making holograms of an object, comprising
    a laser source emitting a collimated or slightly divergent laser beam;
    a holder for a holographic plate to hold said holographic plate between said object and said laser source in a position near said object;
    a positive lens means as the only optical element directly acting on said laser beam and having its focus situated between said lens means and said holographic plate such that a divergent laser beam is impinging on said holographic plate and cover an illuminating area on said plate extending well beyond the area of said object in a plane parallel to said holographic plate;
    a closed housing around said laser source and said lens means; and
    a controllable shutter to be opened only at control provided in an end wall of said housing in a position cutting the beam path of said outgoing laser beam.

2. An apparatus according to claim 1, wherein said shutter is provided as a bottom of a cupformed cavity formed in said end wall of said housing.

3. An apparatus according to claim 1, wherein said laser source comprises a HeNe-laser.

4. An apparatus according to claim 1, wherein means are provided to keep an over pressure inside said housing at least when an exposure of a hologram is to be made.

5. An apparatus according to claim 1, wherein said laser source and said lens means are provided above said holographic plate said laser beam being directed downwardly towards said holographic plate.

6. An apparatus according to claim 1, wherein said holder is adapted to place said holographic plate in a plane oblique to a horizontal plane.

7. An apparatus according to claim 1, wherein said holder is movable in one direction between two distinct positions, and wherein a light source adapted to lighten a hologram already taken is provided parallel to said laser source and lens means giving practically the same divergent beam path, said light source in a plane perpendicular to the movable direction of said holder and at the same distance from the combination of said laser source and lens means as the distance between said two distict positions.

8. An apparatus according to claim 1, wherein said object is mountable on a table, and wherein means are provided to have said object and said holographic plate controllably movable in relation to each other in a cartesian coordinate system and wherein indication means are provided onto which movements in each direction are indicated.

9. An apparatus according to claim 8, wherein said cartesian coordinate system has its x/y-plane parallel to the plane of said holographic plate when it is placed in said holder.

10. An apparatus according to claim 1, wherein when two already taken holograms are going to be compared, the upper hologram is mounted in said holder for the holographic plate and the lower hologram is provided in a holder adapted for said table such that the two holograms are controllably movable in relation to each other.

11. An apparatus according to claim 1, wherein if holograms of the same object are taken on the same object at different times, at least each hologram except one is processed, for instance with bleach, such that all holograms have different colours.

12. An apparatus according to claim 1, wherein said lens means is a gradient-index lens.

* * * * *